(12) United States Patent
Corma Canós et al.

(10) Patent No.: US 10,112,919 B2
(45) Date of Patent: Oct. 30, 2018

(54) METHODS OF PREPARING OXA-BICYCLOALKENE

(71) Applicant: INTERNATIONAL FLAVORS & FRAGRANCES INC., New York, NY (US)

(72) Inventors: Avelino Corma Canós, Valencia (ES); Antonio Leyva-Pérez, Valencia (ES); Estela Espinós Ferri, Castellón (ES); Carlos López Cruz, Castellón (ES)

(73) Assignee: International Flavors & Fragrances Inc., New York, NY (US)

( * ) Notice: Subject to any disclaimer, the term of this patent is extended or adjusted under 35 U.S.C. 154(b) by 0 days.

(21) Appl. No.: 15/838,455

(22) Filed: Dec. 12, 2017

(65) Prior Publication Data

US 2018/0170896 A1    Jun. 21, 2018

(30) Foreign Application Priority Data

Dec. 20, 2016 (EP) .................................... 16382632

(51) Int. Cl.
| | |
|---|---|
| *C07D 311/94* | (2006.01) |
| *C11B 9/00* | (2006.01) |
| *B01J 23/34* | (2006.01) |
| *C07B 33/00* | (2006.01) |
| *C07B 37/10* | (2006.01) |
| *C07D 313/06* | (2006.01) |

(52) U.S. Cl.
CPC ............. *C07D 311/94* (2013.01); *B01J 23/34* (2013.01); *C07B 33/00* (2013.01); *C07B 37/10* (2013.01); *C07D 313/06* (2013.01); *C11B 9/008* (2013.01)

(58) Field of Classification Search
CPC ..................................................... C07D 311/94
USPC ......................................................... 549/396
See application file for complete search history.

(56) References Cited

U.S. PATENT DOCUMENTS 3,856,815 A    12/1974  Hopp et al.

OTHER PUBLICATIONS

Extended European Search Report dated Jun. 21, 2017 for Application No. EP 16382632.4.
Hanaki N et al : "Stereospecific Annulation of Hydroxy Vinyl Ethers. Synthetic Application to Polyfuncti onalized Cyclic Compounds" , Tetrah edron, Elsevi er Sci ence Publishers, Amsterdam, N L, vol . 52, No. 21, May 20, 1996 (May 20, 1996), pp. 7297-7320, XP004103913, ISSN: 0040-4020, DOI: 10.1016/0040-4020(96)00253-0.

*Primary Examiner* — Nizal S Chandrakumar
(74) *Attorney, Agent, or Firm* — Martin Zhang; XuFan Tseng; Elizabeth M. Stover

(57) ABSTRACT

Disclosed is a method of preparing an oxa-bicycloalkene via the reaction of a cycloalkanone and an allyl alcohol compound in the presence of an organic acid, a manganese catalyst, and oxygen at a predetermined temperature.

10 Claims, No Drawings

METHODS OF PREPARING OXA-BICYCLOALKENE

FIELD OF THE INVENTION

The present invention relates to synthesis of oxa-bicycloalkene through the reaction of cycloalkanone and allyl alcohol or its derivatives in the presence of an organic acid, manganese catalyst and oxygen, in particular a one-step process for manufacturing 3,4,5,6,7,8,9,10,11,12,13,14-dodecahydro-2H-cyclododeca[b]pyran (BCP), a compound widely used in the fragrance industry.

BACKGROUND OF THE INVENTION

Oxygenated macrocycles having 12-16 atoms are valuable fragrance ingredients, e.g., 3,4,5,6,7,8,9,10,11,12,13,14-dodecahydro-2H-cyclododeca[b]pyran (BCP; also named 13-oxabicyclo[10.4.0]hexadec-1(12)-ene) and Exaltolide. These compounds are typically manufactured through the common intermediate keto-alcohol as shown in Scheme 1 below.

Scheme 1. Oxygenated macrocycles manufactured through a common intermediate

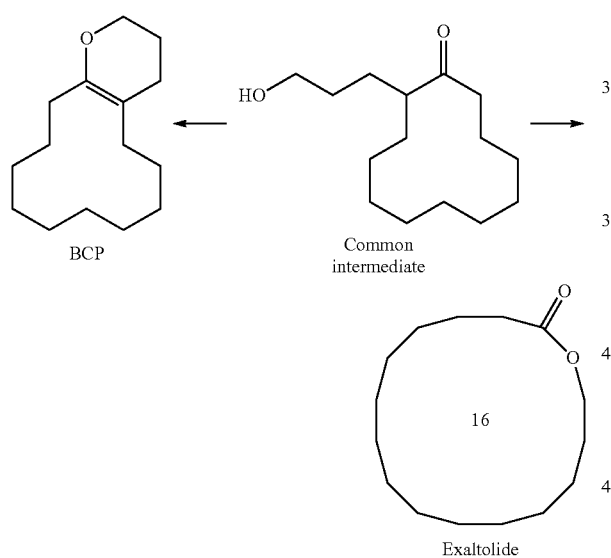

Four different routes have been described in the literature for the synthesis of this intermediate, and subsequently of the target two products.

A first reported route utilizes tert-butyl peroxide in an amount of 15-30 mol % to obtain the keto-alcohol intermediate in a batch reaction with a yield below 25% based on the amount of the starting material cyclododecanone added to the reaction mixture. See U.S. Pat. No. 3,856,815. This process operates at high temperatures (>135° C.) to achieve a reasonable yield. Further, the reactants must be carefully added to the reaction mixture at such a rate that the decomposition of the peroxide and the synthetic reaction couple well, resulting in a low reproducibility of the yield from batch to batch.

A second route involves a cyclization between an imine group and an adjacent alkyl ester group on a dodecane ring with lithium aluminum hydride at a yield of 50%. See Mahajan et al., Synthesis 1980, 1, 64-6. Lithium aluminum hydride is an expensive reagent, which is harmful to the health of plant operators, is explosive during work-up with water, and generates a large amount of hazardous solid waste. As such, the use of the aluminum agent is not cost effective, particularly on a large scale.

A third route follows a three-step process including (i) ketal protection of the ketone, (ii) partial ketal opening with an aluminum reducing agent, and (iii) cyclization with a strong acid to obtain the oxygenated macrocyle product with a yield of 10% or below. For step (iii), see Gassman et al., J. Org. Chem. 1993, 1449-57. The yield from this route is low and the use of the aluminum agent is not cost effective.

A fourth route, illustrated in Scheme 2 below, also includes three steps: (i) preparation of a spiroacetal from dodecanone and a 1,3-diol in the presence of a catalytic amount of p-toluenesulfonic acid or pyridinium p-toluenesulfonate, (ii) obtaining a hydroxyl vinyl ether by deprotonation and ether cleavage of the spiroacetal using triisobutylaluminum, and (iii) forming the oxygenated macrocycle by annulation-elimination of the hydroxyl vinyl ether. See Hanaki et al., Tetrahedron 1996, 52(21), 7297-7320. Apart from the low yield, the route is not cost effective as it uses triisobutylaluminum.

Scheme 2. Synthesis of BCP through a hydroxyl vinyl ether

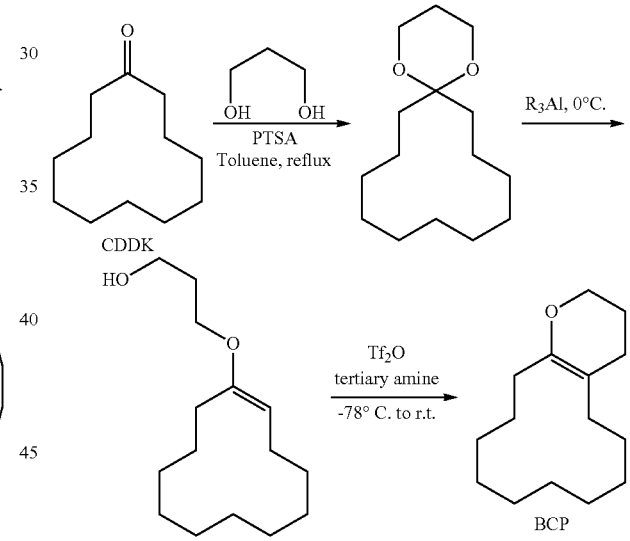

Among the methods described above, only the first one utilizes a one-step synthetic process to prepare the target fragrance compounds. Nevertheless, it requires the consumption of a large amount of hazardous di-tert-butyl peroxide.

There is a need to develop a cost effective, safe process of preparing an oxa-bicyclo alkene in a reasonable yield.

SUMMARY OF THE INVENTION

The present application discloses syntheses of oxa-bicycloalkenes via a one-step process involving the reaction between a cycloalkanone and an allyl alcohol compound in the presence of an organic acid, a manganese catalyst and oxygen at an elevated temperature. The process offers significant cost savings by using reusable manganese catalyst and also an environment-friendly and sustainable synthesis by reducing a large amount of process waste and avoiding use of hazardous and expensive aluminum reagents in traditional routes.

In one aspect, the present invention provides a method of preparing an oxa-bicycloalkene through reacting (i) a cycloalkanone and (ii) an allyl alcohol compound in the presence of an organic acid, a manganese catalyst, and oxygen at a temperature of 60 to 200° C. for 1 to 24 hours.

In one embodiment, the oxa-bicycloalkene has the following Formula (I):

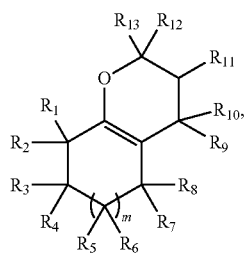

in which m is 0-11 (e.g., 2-10, 6-8, 5, 6, 7, and 8);

each of $R_1$ to $R_{13}$, independently, is H, OH, SH, CN, $NO_2$, $NH_2$, halo (i.e., F, Cl, Br, and I), $C_1$-$C_{10}$ alkyl, $C_2$-$C_{10}$ alkenyl, $C_2$-$C_{10}$ alkynyl, $C_1$-$C_{10}$ heteroalkyl, $C_3$-$C_8$ cycloalkyl, $C_1$-$C_8$ heterocycloalkyl, $C_1$-$C_{10}$ alkoxy, $C_1$-$C_{10}$ alkylthio, $C_1$-$C_{10}$ acyl, $C_1$-$C_{10}$ acyloxy, aryl, aryloxy, arylthio, $C_1$-$C_{10}$ arylalkyl, heteroaryl, heteroaryloxy, heteroarylthio, $C_1$-$C_{10}$ hetero aryl alkyl, $C_1$-$C_{10}$ alkylamino, $C_1$-$C_{20}$ dialkylamino, arylamino, diarylamino, heteroarylamino, diheteroarylamino, $C_1$-$C_{10}$ alkylsulfonyl, arylsulfonyl, heteroarylsulfonyl, $C_1$-$C_{10}$ alkylsulfonamide, arylsulfonamide, heteroarylsulfonamide, $C_1$-$C_{10}$ alkylmercapto, or arylmercapto; and each of cycloalkyl, heterocycloalkyl, aryl, arylalkyl, heteroaryl, and heteroarylalkyl, independently, is unsubstituted or substituted with $C_1$-$C_{10}$ alkyl, $C_2$-$C_{10}$ alkenyl, $C_2$-$C_{10}$ alkynyl, $C_3$-$C_8$ cycloalkyl, $C_1$-$C_8$ heterocycloalkyl, alkoxy, alkylthio, aryl, aryloxy, arylthio, heteroaryl, heteroaryloxy, heteroarylthio, amino, $C_1$-$C_{10}$ alkylamino, dialkylamino, arylamino, diarylamino, heteroarylamino, diheteroarylamino, alkylsulfonyl, arylsulfonyl, heteroarylsulfonyl, alkylsulfonamide, arylsulfonamide, heteroarylsulfonamide, hydroxyl, halogen, mercapto, alkylmercapto, arylmercapto, cyano, nitro, acyl, acyloxy, carboxyl, amido, carbamoyl, or carboxylic ester; and each of alkyl, alkenyl, alkynyl, alkylene, and alkenylene is unsubstituted or substituted with $C_3$-$C_8$ cycloalkyl, $C_1$-$C_8$ heterocycloalkyl, $C_1$-$C_{10}$ alkoxy, alkylthio, aryl, aryloxy, arylthio, heteroaryl, heteroaryloxy, heteroarylthio, amino, $C_1$-$C_{10}$ alkylamino, $C_1$-$C_{20}$ dialkylamino, arylamino, diarylamino, heteroarylamino, diheteroarylamino, $C_1$-$C_{10}$ alkylsulfonyl, arylsulfonyl, heteroarylsulfonyl, $C_1$-$C_{10}$ alkylsulfonamide, arylsulfonamide, heteroarylsulfonamide, hydroxyl, halogen, mercapto, $C_1$-$C_{10}$ alkylmercapto, arylmercapto, cyano, nitro, acyl, acyloxy, carboxyl, amido, carbamoyl, or carboxylic ester.

A specific example of the oxa-bicycloalkene is 3,4,5,6,7,8,9,10,11,12,13,14-dodecahydro-2H-cyclododeca[b]pyran ("BCP") having the following Formula (IV):

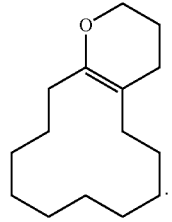

The cycloalkanone typically has 4 to 16 ring atoms selected from carbon, oxygen, sulfur, and nitrogen. Suitable examples include the compounds of Formula (II):

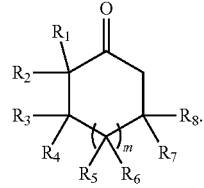

In this formula, m and $R_1$-$R_8$ are defined above. One specific example is CDDK, namely, cyclododecanone of Formula (V):

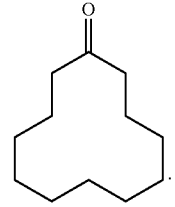

The allyl alcohol compound can be represented by the following Formula (III):

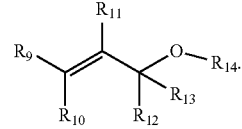

$R_9$-$R_{13}$ are define above. $R_{14}$ is H, $C_1$-$C_{10}$ alkyl, $C_2$-$C_{10}$ alkenyl, $C_2$-$C_{10}$ alkynyl, $C_1$-$C_{10}$ heteroalkyl, $C_3$-$C_8$ cycloalkyl, $C_3$-$C_8$ heterocycloalkyl, $C_1$-$C_{10}$ alkoxy, $C_1$-$C_{10}$ alkylthio, $C_1$-$C_{10}$ acyl, $C_1$-$C_{10}$ acyloxy, aryl, aryloxy, arylthio, $C_1$-$C_{10}$ arylalkyl, heteroaryl, heteroaryloxy, $C_1$-$C_{10}$ heteroarylalkyl, $C_1$-$C_{10}$ alkylamino, $C_1$-$C_{20}$ dialkylamino, arylamino, diarylamino, heteroarylamino, diheteroarylamino, $C_1$-$C_{10}$ alkylsulfonyl, arylsulfonyl, heteroarylsulfonyl, $C_1$-$C_{10}$ alkylsulfonamide, arylsulfonamide, heteroarylsulfonamide, $C_1$-$C_{10}$ alkylmercapto, or arylmercapto.

Suitable allyl alcohol compounds include allyl alcohol ($CH_2$=$CHCH_2OH$) or allyl alcohol derivatives such as an ester (allyl acetate, $CH_2$=$CHCH_2OOCCH_3$), ether, oxime, or silyl.

The organic acid can be acetic acid, which is either a glacial acetic acid having a purity of at least 98%, 99%, 99.5%, or 99.8% (a molar concentration of at least 17 Mol/L, or 17.4 Mol/L), or an acetic acid aqueous solution having a molar concentration of 0.1-6.2 Mol/L (e.g., 0.5-6 Mol/L, 1-5 Mol/L, with a lower limit of 0.1, 0.2, 0.5, 1, and 2 Mol/L and an upper limit of 17.4, 15, 10, 6.3, 6, and 5 Mol/L).

Suitable manganese catalysts include manganese (II) compounds selected from manganese (II) acetate, manganese (II) sulfate, manganese (II) chloride, manganese (II) bromide, manganese (II) iodide, manganese (II) oxide, manganese (II) triflate, and manganese (II) perchlorate. In one embodiment, the manganese catalyst is supported on a zeolite, aluminophosphate, polyoxometallate, or combination thereof. The oxygen can be provided as air, oxygen-enriched air, or oxygen gas in a pressure of 1 to 24 atmospheres.

In some embodiments, the molar ratio between the cycloalkanone and the allyl alcohol compound is 20:1 to 1:6 (e.g., 18:1 to 1:3, 15:1 to 1:2, 12:1 to 1:1, and 10:1 to 2:1), the molar ratio between the organic acid and the allyl alcohol compound is 100:1 to 1:1 (e.g., 50:1 to 2:1, 30:1 to 3:1, and 20:1 to 5:1), and the molar ratio between the manganese catalyst and the allyl alcohol compound is 1:1000 to 1:1 (e.g., 1:500 to 1:2, 1:200 to 1:2, and 1:100 to 1:4).

In some embodiments, the reaction is carried out in a reaction mixture free of a peroxide, an aluminum-based catalyst, or a solvent.

In other embodiments, the reaction is performed in the presence of peracetic acid, the molar ratio between the peracetic acid and the allyl alcohol compound is 1:1 to 100:1, and the peracetic acid is added to the reaction or generated in-situ from the reaction of acetic acid in the presence of the manganese catalyst.

The reaction can be performed in a batch reactor or a continuous reactor system containing a fixed-bed catalyst with the manganese catalyst. Examples of a continuous reactor system include a single Continuous Stirred Tank Reactor (CSTR), a multiple CSTRs in series, or a microreactor.

Other aspects and advantages of the present invention can be better appreciated in view of the detailed description and claims.

DETAILED DESCRIPTION OF THE INVENTION

The present invention is based on surprising discoveries of the versatile utility of inexpensive manganese salts, in particular manganese (II) acetate, in the synthesis of oxa-bicycloalkene by reacting a cycloalkanone and an allyl alcohol compound. The preparations are particularly of interest in the manufacture of fragrance ingredients such as 3,4,5,6,7,8,9,10,11,12,13,14-dodecahydro-2H-cyclododeca[b]pyran ("BCP").

In some embodiments, the preparation is shown in Scheme 3 below.

Scheme 3. Synthesis of oxa-bicycloalkene of Formula (I)

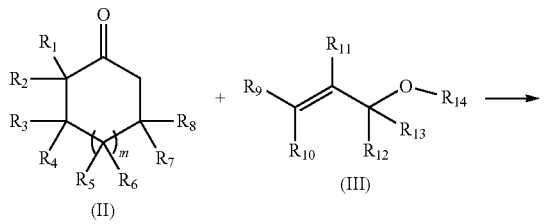

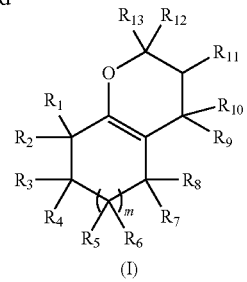

In this scheme, m and $R_1$-$R_{14}$ are defined above. The reaction shown in Scheme 3 is typically carried out in a one-step process without the necessity of separating an intermediate. In general, cycloalkanone of Formula (II) is added to a reaction vessel and mixed with an allyl alcohol compound of Formula (III), together with a manganese catalyst and an organic acid. Oxygen gas is then introduced to the reaction vessel with seal and the reaction is then carried out at a pressure of 0.1 to 24 atmospheres (e.g., 1 to 24 atmospheres and 1 to 12 atmospheres) with a lower limit of 0.1, 0.5, or 1 atmosphere and an upper limit of 24, 22, 20, 18, 16, 15, 12, 10, 9, 8, 6, and 5 atmospheres. Preferably, the reaction vessel is purged with the oxygen gas before the temperature is raised to a predetermine reaction temperature and kept at that temperature for a predetermined period of time to cause the reaction between the cycloalkanone and the allyl alcohol compound. The product of oxa-bicycloalkene can be readily isolated either by distillation or by column chromatography.

The cycloalkanone of Formula (II) can have 4 to 16 atoms, preferably between 10 to 14 atoms, e.g., a macrocyle ketone. The cycloalkanone can be optionally substituted. Namely, each of $R_1$ to $R_8$ independently is a chemical group listed in the summary section above. Preferably, each of $R_1$ to $R_8$, independently, is H, or a lower alkyl having 1 to 6 (e.g., 1 to 4) carbon atoms such as methyl, ethyl, propyl, isopropyl, butyl, isobutyl. In addition, two or more $R_1$ and $R_8$, together with the atom(s) they connect to, can form a ring. As such, the cycloalkanone can be a single ring, fused bicylic ring, fused tricyclic ring, etc. In a preferred embodiment, each of $R_1$ to $R_8$ is H, and the ring has 10, 11, 12, 13, or 14 carbon atoms. Based on the mass of allyl alcohol compound (namely, the mass of the allyl alcohol compound being 1 equivalent), the mass of the cycloalkanone can ranges from 0.2 to 10 equivalents (e.g., 1 to 10 equivalents, and 1 to 4 equivalents) with the lower limit of 0.2, 0.5, 1, or 3 equivalents and the upper limit of 4, 5, 6, 7, 8, or 9 equivalents.

One specific example of this process is the preparation of BCP from cyclododecanone ("CDDK") and allyl acetate (or allyl alcohol) as shown in Scheme 4 below.

Scheme 4. Preparation of BCP

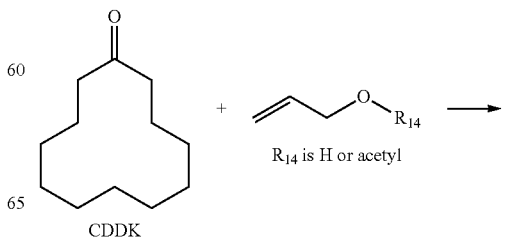

$R_{14}$ is H or acetyl

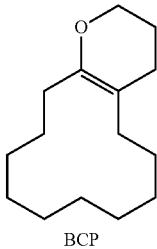

BCP

In some embodiments, the manganese catalyst is a manganese(II) salt in anhydrous or hydrated form, including acetates, sulfates, chlorides, bromides, oxides, triflates, and perchlorates. The manganese catalyst can be supported on a solid such as Mn (II)-zeolites, Mn(II)-aluminophosphates (ALPOs) and Mn(II)-polyoxometallates. Preferably, manganese (II) acetate in hydrated form is used. The mass of the manganese catalyst is 0.1 to 100 mol %, preferably 0.5 to 4 mol % based on the mass of the allyl alcohol compound.

In some embodiments, oxygen is used as air or a pure gas (e.g., containing oxygen at least 80 wt %, at least 85 wt %, at least 90 wt %, at least 95 wt %, at least 98 wt %, at least 99 wt %, at least 99.5 wt %, or at least 99.9 wt %). The oxygen can be added to the reaction mixture at a pressure of 0.1 to 24 atmospheres (e.g., 1 to 12 atmospheres).

Suitable organic acids include acetic acid (AcOH), lactic acid, succinic acid, propionic acid, butyric acid, citric acid, benzoic acid, sorbic acid, tartaric acid, malic acid, gluconic acid, fumaric acid, and combination thereof. A preferred organic acid is acetic acid, e.g., a glacial acetic acid. The organic acid is typically presented in the reaction mixture at a level of 1 to 100 equivalents (e.g., 1 to 5 equivalents) based on the mass of the allyl alcohol compound, with an upper limit of 100, 80, 50, 40, 30, 25, 20, 15, 12, 10, 8, and 5 equivalents.

The reaction is carried out with or without a solvent. Suitable solvents are ethyl acetate, acetonitrile, malononitrile, and combinations thereof.

In some embodiments, the reaction is performed without adding any peroxide compound to the reaction mixture to ensure safety in a manufacturing setting. Peracetic acid may be generated in-situ with manganese catalysts, oxygen and acetic acid. In other embodiments, a relatively safe peroxide such as peracetic acid is added to the reaction mixture in the form of a commercial solution in water/sulfuric acid. The peracetic acid is added to the reaction at a level of 1 to 100 equivalents (e.g., 5 to 10 equivalents) based on the mass of the allyl alcohol compound.

In some embodiments, the reaction is performed at 60 to 200° C. (e.g., 80 to 200° C., and 100 to 130° C.) for a period of 1 to 24 hours (e.g., 2 to 20 hours and 2 to 10 hours) when operating in a batch or semi-continuous mode. If the reaction is performed in a continuous reactor system, the contact time is typically between 0.1 to 10 hours, and preferably 0.5 to 5 hours. The contact time is calculated as the weight of catalyst (g) divided by the flow rate of the starting allyl alcohol compound (g/h) in the continuous reactor.

Herein, this application discloses a convenient and operationally simple means of effecting the cyclization of cycloalkanone with an allyl alcohol compound in a single step using a manganese catalyst, an organic acid, and oxygen.

The results obtained for the coupling of cyclododecanone (CDDK) and one of the two allyl alcohol compounds (e.g., allyl alcohol and allyl acetate) are shown in Table 1 below. These examples showed reactions conducted at various reaction temperatures, reaction time, oxygen pressures, the ratios between the cycloalkanone and allyl alcohol compound, and the molar % of the manganese catalyst based on the mass of the allyl alcohol compound. $Mn(OAc)_2 \cdot 4H_2O$ was used as a catalyst. The yield was calculated based on the allyl alcohol compound. Unexpectedly, BCP was obtained at a high yield (e.g., 45%) and a high selectivity (e.g., 95%). Selectivity refers to the molar percentage of BCP as compared to the mass of the allyl alcohol compound consumed in the reaction.

TABLE 1

Preparation of BCP

| Example | Allyl | Ratio[d] | Mn (mol %) | $O_2$ (atm) | T (° C.) | Time (h) | Yield (%) | S (%) |
|---|---|---|---|---|---|---|---|---|
| 1[a] | OH | 4:1 | 25 | 1 | 80 | 4 | 13 | >95 |
| 2 | OAc | 4:1 | 25 | 1 | 80 | 4 | 22 | 73 |
| 3 | OAc | 10:1 | 2.5 | 10 | 110 | 4 | 39 | 88 |
| 4 | OAc | 10:1 | 2.5 | 10 | 110 | 4 | 42 | 87 |
| 5 | OAc | 10:1 | 0.5 | 10 | 110 | 18 | 45 | 90 |
| 6[a] | OH | 10:1 | 2.5 | 10 | 110 | 4 | 15 | >95 |
| 7[b] | OAc | 4:1 | 1 | 10 | 110 | 9 | 37 | 88 |
| 8[c] | OAc | 2:1 | 1 | 10 | 110 | 5 | 29 | 85 |
| 9[c] | OAc | 4:1 | 1 | 10 | 110 | 5 | 33 | 89 |
| 10[c] | OAc | 2:1 | 1 | 10 | 130 | 3.5 | 29 | 88 |
| 11[c] | OAc | 4:1 | 1 | 10 | 130 | 3.5 | 41 | 87 |

[a]By-products from alcohol oxidation were found.
[b]AcOH (5M).
[c]AcOH (2M).
[d]Molar ratio CDDK/allyl alcohol compound.
[e] Glacial AcOH is used in Examples 1-6.

Only a catalytically effective amount of manganese catalyst is required for the reaction. In addition, the manganese catalyst is much safer to handle than the peroxides used in traditional processes of preparing BCP. See U.S. Pat. No. 3,856,815. The reaction temperature is kept moderate at 80 to 130° C.

The manganese catalyst can be reused. Catalyst $Mn(OAc)_2 \cdot 4H_2O$, as used in these examples, is soluble in the reaction medium. It was quantitatively recovered after distillation of the reaction mixture or by precipitation with a non-polar solvent (e.g., hexane, ether, and dichloromethane). Without any additional treatment, the manganese acetate so recovered was reused in the reaction without loss of its catalytic activity.

In addition, $Mn(OAc)_2 \cdot 4H_2O$ can be supported on a solid in order to get a filterable catalyst, and/or amenable for a continuous flow process. Preferentially, Mn(II) acetate hydrate is incorporated on $\gamma$-$Al_2O_3$, silica, titania or zirconia by impregnation, or on 12R pore zeolites (e.g., H-Y zeolite commercially available as CBV-720 and CBV-740 from Zeolyst International, Valley Forge, Pa.; HBeta zeolite commercially available as CP811C-300 from Zeolyst International; and mordenite zeolite commercially available as CBV10A and CBV21A from Zeolyst International) by the exchange method to obtain, for instance, a $Mn^{2+}$-HBeta zeolite. Other solid supports include ALPOs and polyoxometallates. These solid-supported catalysts effectively catalyze the reaction and can be readily recovered from the reaction mixture by simple filtration.

The term "alkyl," as used herein, means a straight or branched-chain saturated hydrocarbon group containing from 1 to 10 carbon atoms, preferably 1 to 8 carbon atoms, more preferably 1 to 6 carbon atoms ("lower alkyl"), and even more preferably 1 to 4 carbon atoms, which is connected with the rest of the molecular moiety through a single bond. Representative examples include, but are not limited to, methyl, ethyl, n-propyl, iso-propyl, n-butyl, sec-butyl, iso-butyl, tert-butyl, etc.

The term "alkoxy," as used herein, means an "—O-alkyl" group, where alkyl is as defined herein. Representative examples of alkoxy include methoxy, ethoxy, propoxy, 2-propoxy, butoxy, tert-butoxy, etc.

The term "aryl," as used herein, means an aromatic hydrocarbon group composed of 6 to 14, preferably 6 to 10, carbon atoms. Representative examples of aryl include phenyl and naphthyl. Unless specified in the present application, the term "aryl" may be substituted by one or more substituents, such as $C_1$-$C_6$ alkyl, $C_1$-$C_6$ haloalkyl, $C_1$-$C_6$ alkoxy, etc.

The term "arylalkyl" refers to an alkyl group substituted by one or more aryl groups, wherein alkyl and aryl are as defined herein. Representative examples of arylalkyl include, but are not limited to, benzyl, 2-phenylethyl, diphenylmethyl, and naphth-2-ylmethyl, etc.

The term "carboxyl," as used herein, means a —C(O)O⁻ or —$CO_2$H group.

The term "cycloalkyl," as used herein, means a cyclic hydrocarbon group containing from 3 to 24 carbon atoms (e.g., 3 to 20, and 5 to 18 carbon atoms), where such groups can be saturated or unsaturated, but not aromatic. In certain embodiments, cycloalkyl groups are preferably fully saturated. Examples of cycloalkyl include, but are not limited to, cyclopropyl, cyclobutyl, cyclopentyl, cyclohexyl, cyclohexenyl, etc.

The term "cycloalkylalkyl," as used herein, means alkyl group substituted by one or more cycloalkyl group, wherein alkyl and cycloalkyl are as defined herein.

The term "acyl" or "acylated" means —C(O)$R^5$, where $R^5$ is defined above.

The term "halo" or "halogen" refers to F, Cl, Br, and I, preferably Cl or Br.

The term "haloalkyl" refers to an alkyl group substituted by one or more halogen atoms.

The singular forms "a", "an", and "the" include plural reference, and vice versa, unless the context clearly dictates otherwise.

The term "about," when used in front of a number, indicates that the number can fluctuate for ±10%, preferably within ±5%. The values and dimensions disclosed herein are not to be understood as being strictly limited to the exact numerical values recited. Instead, unless otherwise specified, each such value is intended to mean both the recited value and a functionally equivalent range surrounding that value. For example, a value disclosed as "50%" is intended to mean "about 50%."

All parts, percentages and proportions refer to herein and in the claims are by weight unless otherwise indicated.

The terms "g," "mg," and "µg" refer to "gram," "milligram," and "microgram," respectively. The terms "L" and "mL" refer to "liter" and "milliliter," respectively. The term "Mol" and "mmol" refer to "mole" and millimole," respectively.

The invention is described in greater detail by the following non-limiting examples. Without further elaboration, it is believed that one skilled in the art can, based on the description herein, utilize the present invention to its fullest extent.

EXAMPLES

General Reaction Procedure.

A predetermined amount of Mn(II) catalyst and cyclododecanone (e.g., 12 mmol) were added to a 6-mL vial equipped with a magnetic stirrer. Acetic acid (AcOH; 1 mL) and the allyl alcohol compound (allyl alcohol or allyl acetate) were then added and the vial was sealed and connected to a manometer. Oxygen was introduced through a valve to reach a predetermined pressure (1 to 24 atmospheres) and then liberated to purge the vial. This operation was repeated twice to finally leave the required oxygen atmosphere (c.a. 1 to 6 mmol). The vial was placed in an oil-bath at a predetermined temperature and stirred for a predetermined period of time. Subsequently, the vial was cooled, the remaining oxygen was liberated, and the mixture was analyzed by a gas chromatography ("GC") after dilution in dichloromethane. The product was isolated either by distillation or by flash column chromatography on silica gel, eluting with hexanes-ethyl acetate mixtures.

The desired product BCP was isolated and characterized with GC-MS, $^1$H NMR, and $^{13}$C NMR after column chromatography. Rf (hexane-EtOAc, 4:1)=0.75. GC-MS, m/z 222.2 [M]$^+$. $^1$H NMR (CDCl$_3$, 300 MHz; δ in ppm, J in Hz): 3.89 (t, J=5.0, 2H), 2.16 (t, J=6.7, 2H), 2.03 (t, J=7.0, 2H), 1.94 (t, J=6.3, 2H), 1.83 (quint, J=5.7, 2H), 1.45-1.20 (mult, 16H). $^{13}$C NMR (CDCl$_3$, 75 MHz; δ in ppm): 148.5 (C), 107.0 (C), 65.5 (CH$_2$), 37.0 (CH$_2$), 30.5-21.8 (11×CH$_2$).

The major impurity of the reaction was 3-(2-oxocyclodecyl)propyl acetate, which was confirmed by $^1$H NMR and $^{13}$C NMR analysis.

Examples 1-9

BCP was prepared following the general procedure with the amount of reagents indicated in Table 1 above, Examples 1-9, respectively.

Example 10

Reaction Procedure for Example 10 Shown in Table 1.

Mn(OAc)$_2$.4H$_2$O (2.8 mg, 1 mol %) and CDDK (430 mg, 2.4 mmol) were added to a 6-mL vial equipped with a magnetic stirrer. AcOH (0.5 mL) and allyl acetate (128 µL, 1.2 mmol) were then added and the vial was sealed, connected to a manometer. Oxygen was introduced through a valve to reach 10 atmospheres and liberated to purge the vial. This operation was repeated twice to finally fill the vial with oxygen at a pressure of 10 atmospheres (about 3 mmol). The vial was placed in an oil-bath at 130° C. and stirred for 3.5 h. After that, the vial was cooled, the remaining oxygen was liberated, and the mixture was analyzed by GC after dilution in dichloromethane.

Example 11

Reaction Procedure for Example 11 Shown in Table 1.

MnOAc)$_2$.4H$_2$O (2.8 mg, 1 mol %) and CDDK (860 mg, 4.8 mmol for 4:1) were added to a 6-mL vial equipped with a magnetic stirrer. After AcOH (0.5 mL) and allyl acetate (128 µL, 1.2 mmol) were added, the vial was sealed, connected to a manometer, and purged with oxygen twice. Subsequently, the vial was filled with oxygen at a pressure of 10 atmospheres (about 3 mmol) and heated in an oil-bath at 130° C. for 3.5 hours. After that, the vial was cooled, remaining oxygen liberated, and the mixture was analyzed by GC after dilution in dichloromethane.

All references cited herein are incorporated by reference in their entirety. The foregoing examples and description of certain preferred embodiments should be taken as illustrating, rather than as limiting, the present invention. As would be readily appreciated by a person skilled in the art, numerous variations and combinations of the features set forth above can be utilized without departing from the present invention, which are all encompassed by the present invention.

What is claimed is:

1. A method of preparing an oxa-bicycloalkene comprising reacting (i) a cycloalkanone and (ii) an allyl alcohol compound in the presence of an organic acid, a manganese catalyst, and oxygen at a temperature of 60 to 200° C. for 1 to 24 hours, wherein the oxa-bicycloalkene is 3,4,5,6,7,8,9,10,11,12,13,14-dodecahydro-2H-cyclododeca[b]pyran having the following Formula (IV):

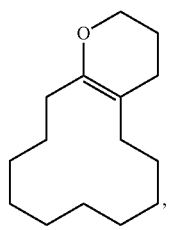
(IV)

the cycloalkanone is cyclododecanone of Formula (V):

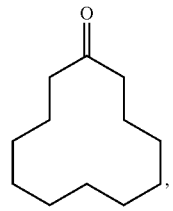
(V)

and
the allyl alcohol compound is allyl acetate or allyl alcohol.

2. The method of claim 1, wherein the organic acid is acetic acid, and the manganese catalyst is a manganese (II) compound selected from the group consisting of manganese (II) acetate, manganese (II) sulfate, manganese (II) chloride, manganese (II) bromide, manganese (II) iodide, manganese (II) oxide, manganese (II) triflate, and manganese (II) perchlorate.

3. The method of claim 2, wherein the manganese catalyst is supported on a zeolite, aluminophosphate, polyoxometallate, or combination thereof.

4. The method of claim 1, wherein the molar ratio between the cycloalkanone and the allyl alcohol compound is 20:1 to 1:6, the molar ratio between the organic acid and the allyl alcohol is 100:1 to 1:1, and the molar ratio between the manganese catalyst and the allyl alcohol is 1:1000 to 1:1.

5. The method of claim 1, wherein the reaction is performed in the presence of peracetic acid, the molar ratio between the peracetic acid and the allyl alcohol compound is 1:1 to 100:1, and the peracetic acid is added to the reaction or generated in-situ from the reaction of acetic acid in the presence of the manganese catalyst.

6. The method of claim 1, wherein the oxygen is provided as air, oxygen-enriched air, or oxygen gas in a pressure of 1 to 24 atmospheres.

7. The method of claim 1, wherein the reaction is performed in the absence of a solvent.

8. The method of claim 1, wherein the reaction is performed in a batch reactor or a continuous reactor system.

9. The method of claim 8, wherein the reaction is performed in a continuous reactor system, and the manganese catalyst is a fixed-bed catalyst.

10. The method of claim 9, wherein the continuous reactor system is a single Continuous Stirred Tank Reactor (CSTR), a multiple CSTRs in series, or a microreactor.

* * * * *